(12) United States Patent
Wilson

(10) Patent No.: US 12,268,360 B2
(45) Date of Patent: Apr. 8, 2025

(54) MANUAL HEXAPOD LOCKING MECHANISM

(71) Applicant: Medtronic Navigation, Inc., Louisville, CO (US)

(72) Inventor: Drew Wilson, Louisville, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 309 days.

(21) Appl. No.: 17/745,283

(22) Filed: May 16, 2022

(65) Prior Publication Data

US 2023/0363626 A1   Nov. 16, 2023

(51) Int. Cl.
*A61B 1/00* (2006.01)
*A61B 17/60* (2006.01)
*A61B 34/30* (2016.01)
*A61B 17/00* (2006.01)

(52) U.S. Cl.
CPC ...... *A61B 1/00154* (2013.01); *A61B 1/00149* (2013.01); *A61B 1/0016* (2013.01); *A61B 17/00234* (2013.01)

(58) Field of Classification Search
CPC ............ A61B 1/00154; A61B 1/00149; A61B 1/0016; A61B 17/00234; A61B 17/6433; A61B 2034/304; A61B 90/11; A61B 17/62; A61B 8/4209; F16C 11/06; F16M 2200/022; F16M 2200/024
USPC ....................................................... 600/146
See application file for complete search history.

(56) References Cited

U.S. PATENT DOCUMENTS

| | | | |
|---|---|---|---|
| 4,620,813 A * | 11/1986 | Lacher | F16C 11/106 403/93 |
| 5,592,939 A | 1/1997 | Martinelli | |
| 5,913,820 A | 6/1999 | Bladen et al. | |
| 5,983,126 A | 11/1999 | Wittkampf | |
| 6,235,038 B1 | 5/2001 | Hunter et al. | |
| 6,530,688 B1 * | 3/2003 | Muller | B25J 17/0216 378/197 |
| 7,751,865 B2 | 7/2010 | Jascob et al. | |
| 7,803,164 B2 | 9/2010 | Gielen et al. | |
| 8,010,177 B2 | 8/2011 | Csavoy et al. | |
| 8,644,907 B2 | 2/2014 | Hartmann et al. | |

(Continued)

FOREIGN PATENT DOCUMENTS

CN    205094509 U    3/2016

OTHER PUBLICATIONS

International Search Report and Written Opinion ISR/WO, corresponding to PCT/IB2023/054750, Date of Mailing: Aug. 25, 2023, EPO/SA.

(Continued)

*Primary Examiner* — Anh Tuan T Nguyen
*Assistant Examiner* — Rynae E Boler
(74) *Attorney, Agent, or Firm* — Harness, Dickey & Pierce, P.L.C.

(57) ABSTRACT

A surgical alignment device including a base, a guide, and a plurality of linear actuators each extending between the base and the guide. The plurality of linear actuators include first ends connected to the base at base joints and second ends connected to the guide at guide joints. A locking arrangement is configured to simultaneously lock all of the base joints or simultaneously lock all of the guide joints.

19 Claims, 8 Drawing Sheets

(56) References Cited

U.S. PATENT DOCUMENTS

| | | | |
|---|---|---|---|
| 8,886,331 B2* | 11/2014 | Labadie | A61N 1/0541 607/57 |
| 9,205,566 B2 | 12/2015 | Schwab | |
| 9,737,235 B2 | 8/2017 | Hartmann | |
| 9,764,466 B2 | 9/2017 | Rey et al. | |
| 9,867,667 B2 | 1/2018 | Fujimoto et al. | |
| 10,194,890 B2 | 2/2019 | Cosgrove et al. | |
| 2009/0036890 A1 | 2/2009 | Karidis | |
| 2010/0137680 A1* | 6/2010 | Nishikawa | A61B 34/70 600/102 |
| 2011/0118738 A1* | 5/2011 | Vasta | A61B 17/62 606/56 |
| 2014/0058389 A1* | 2/2014 | Singh | A61B 17/62 606/56 |
| 2014/0066700 A1 | 3/2014 | Wilson et al. | |
| 2014/0066701 A1* | 3/2014 | Wilson | A61B 1/000094 600/102 |
| 2014/0350572 A1* | 11/2014 | Elhawary | A61B 90/11 606/130 |
| 2015/0305776 A1* | 10/2015 | Ross | A61B 17/60 606/56 |
| 2018/0116758 A1 | 5/2018 | Schlosser et al. | |
| 2018/0279992 A1 | 10/2018 | Frankel et al. | |
| 2019/0029727 A1 | 1/2019 | Park et al. | |

OTHER PUBLICATIONS

Grosch Patrick: "Parallel Robots With Unconventional Joints to Achieve Under-Actuation and Reconfigurability", Jun. 1, 2016 (Jun. 1, 2016), XP093074458, Retrieved from the Internet: URL:http://www.iri.upc.edu/files/academic/thesis/22-Thesis.pdf [retrieved on Aug. 17, 2023] p. 34—p. 38; figure 3.3.

* cited by examiner

MANUAL HEXAPOD LOCKING MECHANISM

FIELD

The present disclosure relates to an alignment guide, such as an alignment guide including a manual hexapod locking mechanism.

BACKGROUND

This section provides background information related to the present disclosure, which is not necessarily prior art.

Surgical procedures are performed on various portions of an anatomy, such as a human anatomy. The surgical procedures can be invasive to varying degrees, such as by performing an open procedure or by performing a less invasive procedure. A procedure can be performed in a less invasive manner by minimizing or attempting to minimize an incision or portal formed in the tissue of the anatomy, opening through bone, and other minimization techniques.

A less invasive procedure, however, can also reduce visualization of a portion of the anatomy upon which a procedure is occurring, reduce access with various instruments to a portion of the anatomy, and the like. The less invasive procedure may also require specialized and particular instruments to perform a procedure in an appropriate and beneficial manner. It is desirable, therefore, to provide instruments, procedures, and the like to achieve an optimal outcome while maintaining the less invasive procedure.

While current surgical alignment devices are suitable for their intended use, they are subject to improvement. The present disclosure advantageously includes improved alignment devices that address various needs in the art. For example, the alignment devices of the present disclosure facilitate freehand alignment of a surgical instrument, such as aligning to a biopsy plan and target.

SUMMARY

This section provides a general summary of the disclosure, and is not a comprehensive disclosure of its full scope or all of its features.

The present disclosure provides for a surgical alignment device including a base, a guide, and a plurality of linear actuators each extending between the base and the guide. The plurality of linear actuators including first ends connected to the base at base joints and second ends connected to the guide at guide joints. A locking arrangement is configured to simultaneously lock all of the base joints or simultaneously lock all of the guide joints.

The present disclosure further provides for a surgical alignment device including a base, a guide, and a plurality of linear actuators each extending between the base and the guide. The plurality of linear actuators include first ends connected to the base at base joints and second ends connected to the guide at guide joints. Base brakes are at each one of the base joints. Guide brakes are at each one of the guide joints. A base locking ring is included with the base and is in cooperation with the base brakes such that rotation of the base locking ring in a first direction moves the base brakes into engagement with the plurality of linear actuators to lock the base joints. Rotation of the base locking ring in a second direction opposite to the first direction releases the base brakes from engagement with the plurality of linear actuators to unlock the base joints. A guide locking ring is included with the guide and is in cooperation with the guide brakes such that rotation of the guide locking ring in a first direction moves the guide brakes into engagement with the plurality of linear actuators to lock the guide joints. Rotation of the guide locking ring in a second direction opposite to the first direction releases the guide brakes from engagement with the plurality of linear actuators to unlock the guide joints.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of select embodiments and not all possible implementations, and are not intended to limit the scope of the present disclosure.

Corresponding reference numerals indicate corresponding parts throughout the several views of the drawings.

DETAILED DESCRIPTION

Figure 1A:
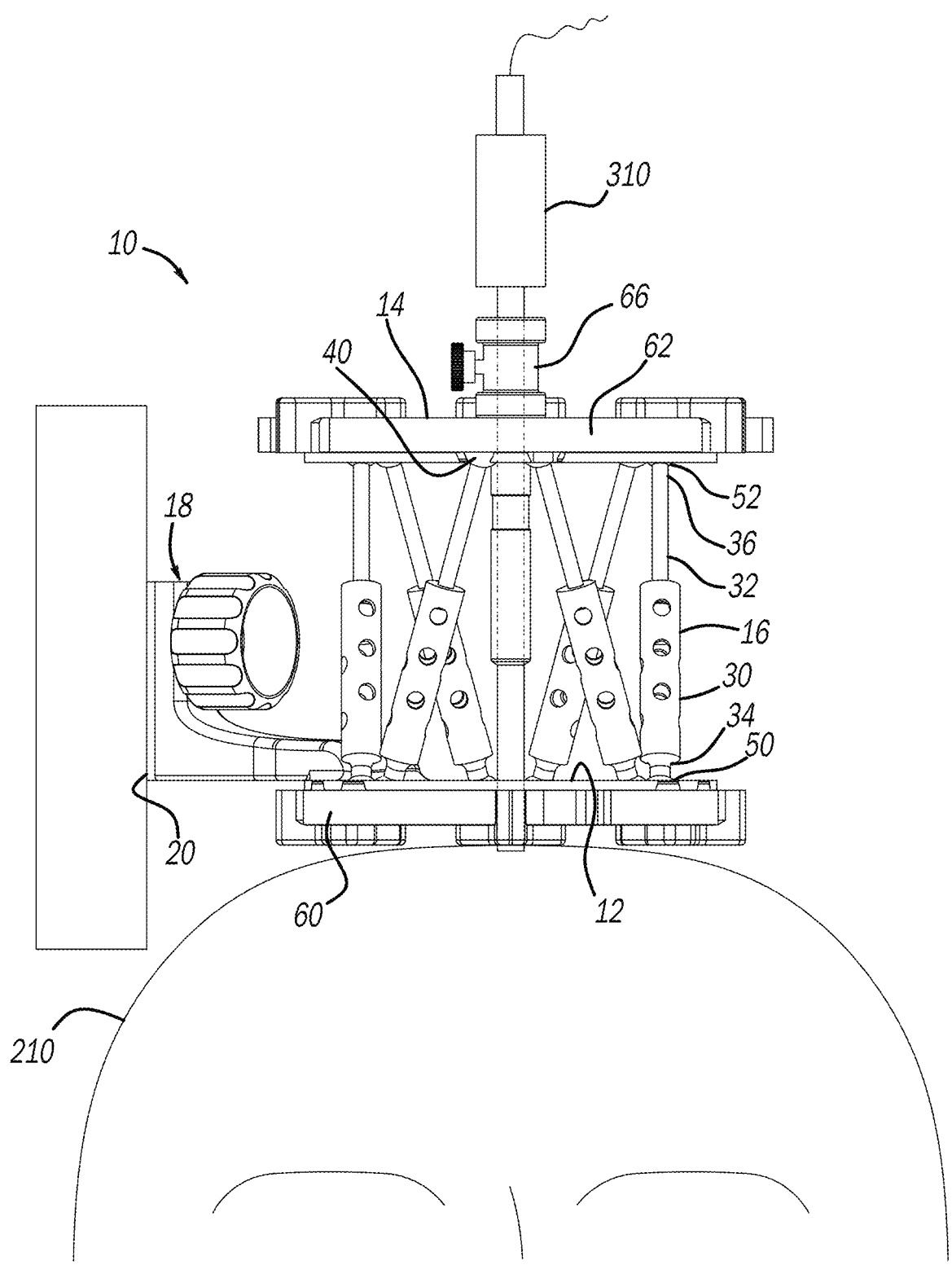
FIG. 1A is a side view of a surgical alignment device in accordance with the present disclosure mounted at an exemplary surgical site.

Example embodiments will now be described more fully with reference to the accompanying drawings.

With initial reference to FIGS. 1A-6, an exemplary surgical alignment device in accordance with the present disclosure is illustrated at reference numeral 10. The surgical alignment device 10 may be used in any suitable surgical or non-surgical procedure. With respect to surgical procedures, the device 10 may be used with any navigated procedure requiring alignment of an instrument to a trajectory, or for holding of an instrument in a fixed position. Exemplary surgical procedures include, but are not limited to, biopsy procedures, spinal procedures, cranial procedures, etc.

Instruments, according to various applications, can be guided with the device 10 to a selected portion of the anatomy to perform a procedure in a less invasive manner. For example, a scope can be guided along a selected portion of the anatomy for viewing an internal structure within the anatomy. Various other instruments can also be guided by the guide 10 into the anatomy for various procedures. For example, in micro-electrode recording (MER) a micro-electrode (ME) can be guided into a portion of the anatomy, such as the brain, to record electrical activity therein. The recording of the electrical activity can be used for various diagnoses and identification procedures. A probe or deep brain stimulation (DBS) electrode or macro stimulation probe or lead can be guided in an area relative to the ME.

The following description is merely exemplary in nature and is not intended to limit the present disclosure, application, or uses. Moreover, although the following description is related to a procedure performed within a brain of a patient, the procedure within the brain is merely exemplary. Further, use of micro-electrodes for recording, deep brain stimulation probes (also referred to as leads or electrodes), biopsy needles, and the like within the brain are also merely exemplary. It will be understood that the disclosure herein can be used in any appropriate portion of the anatomy and during any appropriate procedure with any appropriate instrument.

A navigation system generally allows for determining a position (e.g., pose) of an instrument relative to a subject in subject space. This is performed with a tracking system. In various embodiments an EM tracking system may be used and may include the STEALTHSTATION® AXIEM™ Navigation System, sold by Medtronic Navigation, Inc. having a place of business in Louisville, Colorado. Exemplary tracking systems are also disclosed in U.S. Pat. No. 8,644,907, issued Feb. 4, 23012, titled "Method And Apparatus For Surgical Navigation"; U.S. Pat. No. 7,751,865, titled "Method And Apparatus For Surgical Navigation", issued Jul. 6, 2010; U.S. Pat. No. 5,913,820, titled "Position Location System," issued Jun. 22, 1999 and U.S. Pat. No. 5,592,939, titled "Method and System for Navigating a Catheter Probe," issued Jan. 14, 1997, all incorporated by reference herein.

A tracking system may also and/or alternatively include any appropriate tracking system, including a STEALTHSTATION® TRIA®, TREON®, and/or S7™ Navigation System having an optical localizer, such as any optical localizer sold by Medtronic Navigation, Inc. having a place of business in Louisville, Colorado. Optical tracking systems may also include those discloses in U.S. Pat. No. 8,010,177, Aug. 30, 2011, Intraoperative Image Registration"; U.S. Pat. No. 6,235,038, issued on May 22, 2001, titled "System For Translation Of Electromagnetic And Optical Localization Systems", all incorporated herein by reference. Further alternative tracking systems are disclosed in U.S. Pat. No. 5,983,126, to Wittkampf et al. titled "Catheter Location System and Method," issued Nov. 9, 1999, which is hereby incorporated by reference. Other tracking systems include an acoustic, radiation, radar, etc. tracking or navigation systems.

A registration of the subject (e.g., navigated or procedure) space to an image space may allow the tracked pose of the instrument to be illustrated relative to an image. According to various embodiments, registration can occur by determining points that are substantially identical in the image space and the patient space. The identical points can include anatomical fiducial points or implanted fiducial points. Exemplary registration techniques are disclosed in U.S. Pat. No. 9,737,235, issued Aug. 22, 2017, incorporated herein by reference.

FIG. 1A illustrates the surgical alignment device 10 mounted at an exemplary surgical site 210 including a human skull and brain. The device 10 is configured to guide any suitable surgical instrument or implant 310 to any suitable location of the skull and brain, for example, at any suitable angle. The surgical instrument 310 may be, for example, any suitable probe, electrode, etc. including those instruments listed above, for example, and those described in, for example, U.S. Pat. No. 7,803,164 titled "Method for Guiding Instruments Having Different Sizes," assigned to Medtronic, Inc. of Minneapolis, Minnesota, the entirety of which is incorporated herein by reference. An exemplary surgical procedure including the device 10 is described further herein.

The surgical alignment device 10 generally includes a base 12, a guide 14, and a plurality of linear actuators 16 extending between the base 12 and the guide 14. The device 10 further includes a connector 18 for mounting the device 10 at any suitable surgical site, or any other location where instrument alignment is desired. The connector 18 includes a bracket 20 supporting any suitable fastener 22. The fastener 22 may be any fastener suitable for securing the surgical alignment device 10 to any suitable jig or other mount.

The linear actuators 16 advantageously provide six degrees of freedom movement of the guide 14 relative to the base 12, as described further herein. Any suitable number of linear actuators 16 may be included with the device 10. For example and as illustrated, the device 10 includes six linear actuators 16. Each one of the linear actuators 16 is the same or substantially similar.

Each one of the linear actuators 16 is generally a slidable link including a cylinder 30 with a piston rod 32 seated therein. The piston rod 32 is slidably movable into and out of the cylinder 30 to vary the distance that the piston rod 32 extends out of the cylinder 30. Depending on the application, the piston rod 32 may be biased inward or outward in any suitable manner, such as with a spring or any other suitable biasing member. Actuation of the piston rod 32 is not controlled in any way other than through manual manipulation of the guide 14 by a user relative to the base 12. Each one of the linear actuators 16 includes a first end 34 and a second end 36, which is opposite to the first and 34. At the first end 34 is a base sphere 38 (see FIGS. 1, 4, 5, 7A, and 7B for example), which is adjacent to the cylinder 30. At the second end 36 is a guide sphere 40 (see FIGS. 2, 3, 5, and 6, for example). The guide sphere 40 is at a distal end of the piston rod 32. The base sphere 38 cooperates with the base 12 at a base joint 50. The guide sphere 40 cooperates with the guide 14 at a guide joint 52.

A base locking ring 60 surrounds the base 12. Both the base locking ring 60 and the base 12 are circular, or substantially circular. Similarly, a guide locking ring 62 surrounds the guide 14. Both the guide locking ring 62 and the guide 14 are circular, or substantially circular. At a center of the guide 14 is an aperture 64. The aperture 64 is configured to receive any suitable instrument guide, such as the instrument guide 66 of FIGS. 2-6. The instrument guide 66 is configured to direct any suitable instrument or implant to a desired surgical site.

The base locking ring 60 is rotatably coupled to the base 12. The base locking ring 60 is rotatable about the base 12 in both a first direction and a second direction, which is opposite to the first direction. The base locking ring 60 includes a plurality of base tabs 70, which may be pushed by a user to rotate the base locking ring 60. Spaced apart about the base 12 are stationary base stops 72. The base locking ring 60 is rotatable in the first direction until at least one of the base tabs 70 contact an adjacent base stop 72. The base stops 72 are positioned such that when one (or more) of the base tabs 70 contacts a base stop 72, there is always another base tab 70 that is spaced apart from a different base stop 72. The base tab 70 spaced apart from the different base stop 72 may be pushed to rotate the base locking ring 60 in the second (opposite) direction.

Figure 1B:
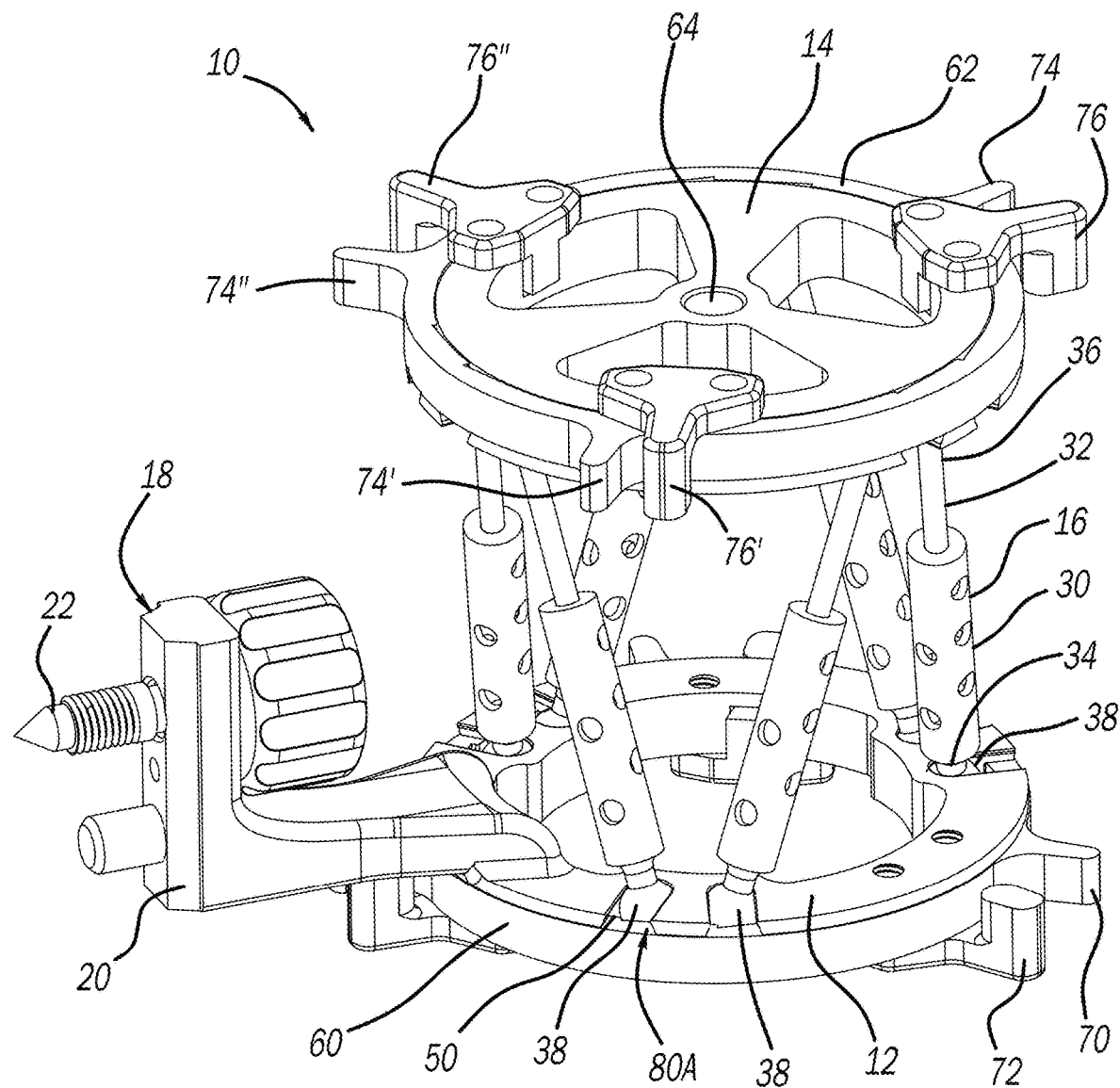
FIG. 1B is a perspective view of the alignment device of FIG. 1A.
Figure 2:
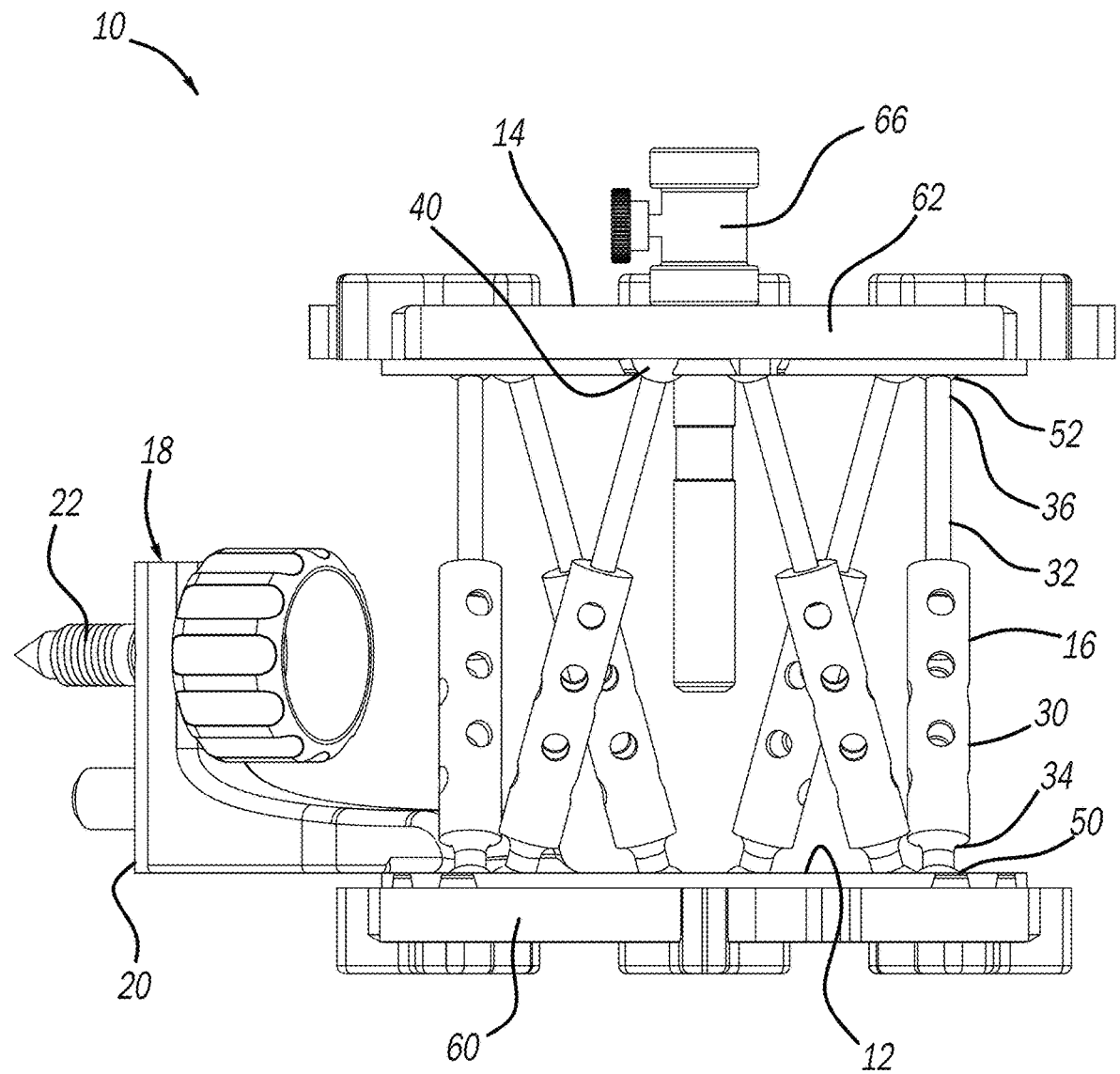
FIG. 2 is a side view of the alignment device of FIG. 1A.
Figure 3:
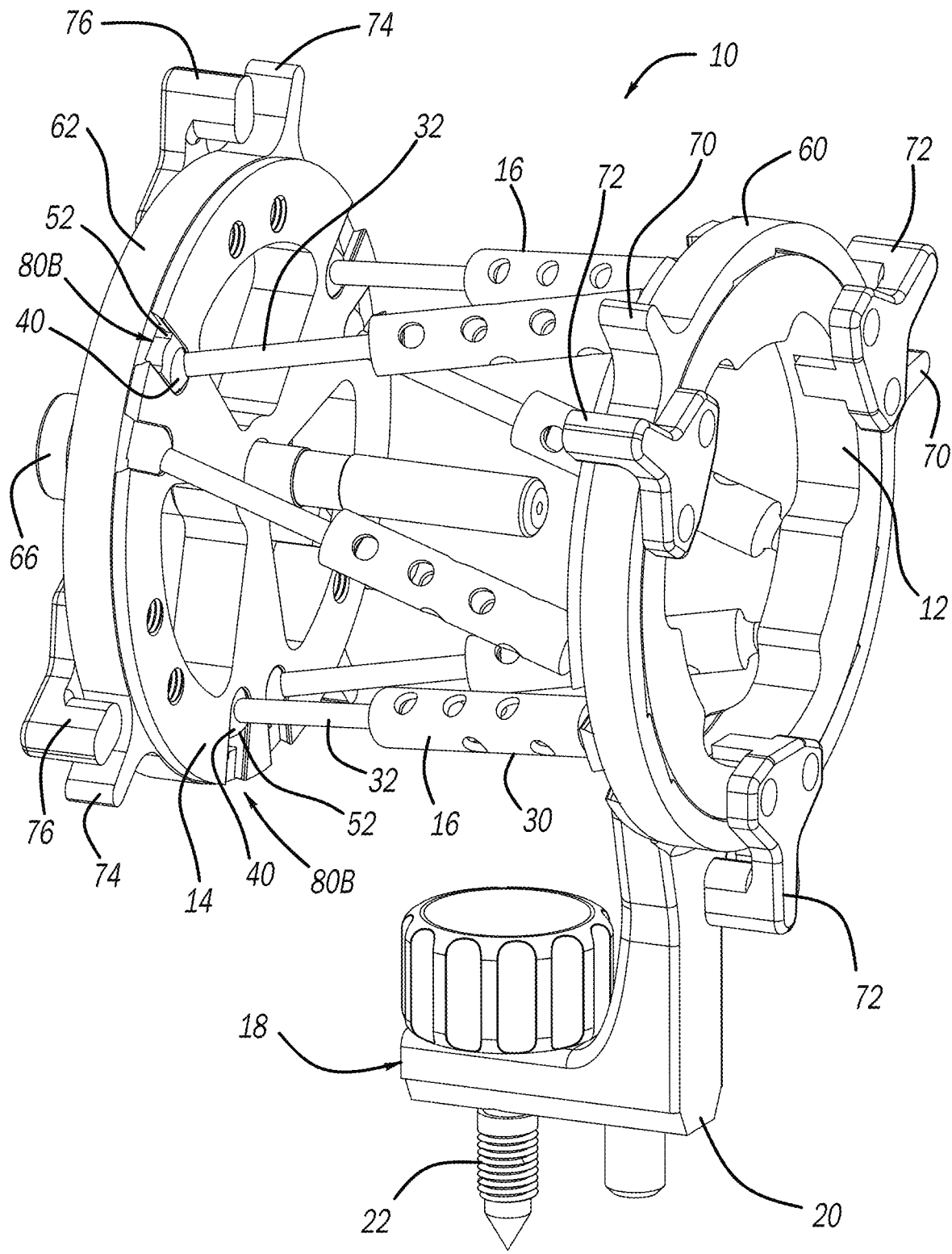
FIG. 3 is another perspective view of the alignment device of FIG. 1A.
Figure 4:
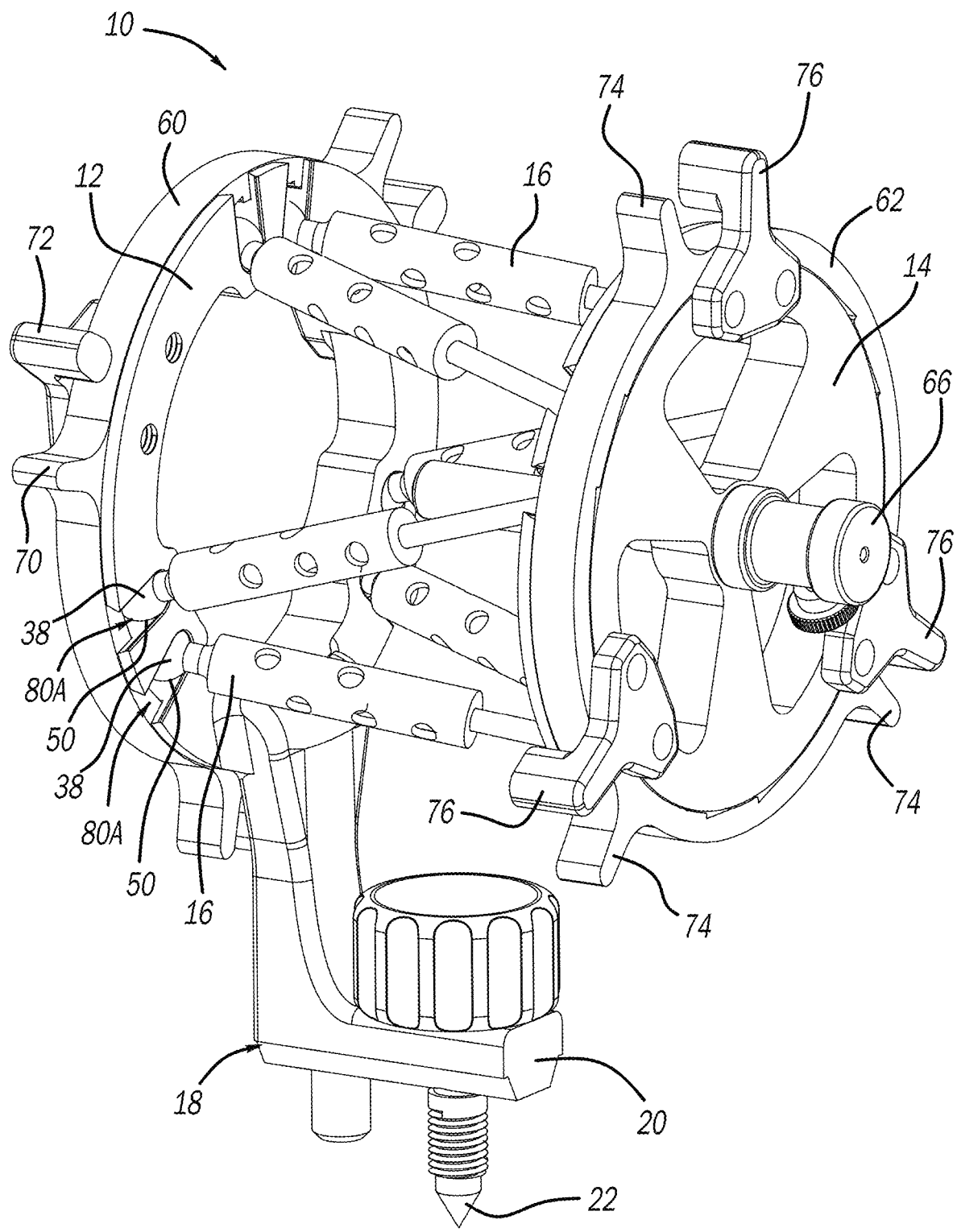
FIG. 4 is an additional perspective view of the alignment device of FIG. 1A.
Figure 5:
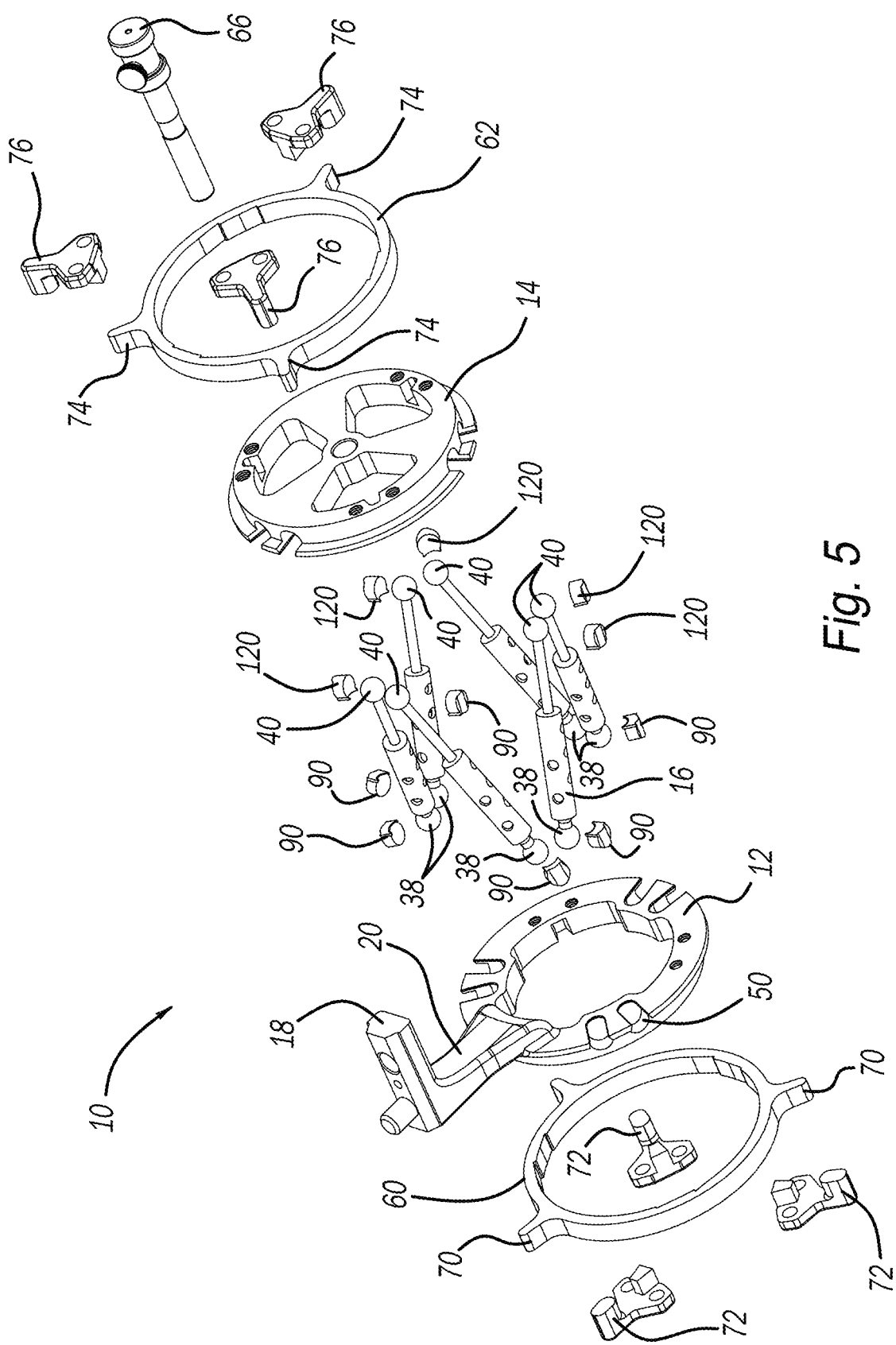
FIG. 5 is an exploded view of the alignment device of FIG. 1A.
Figure 6:
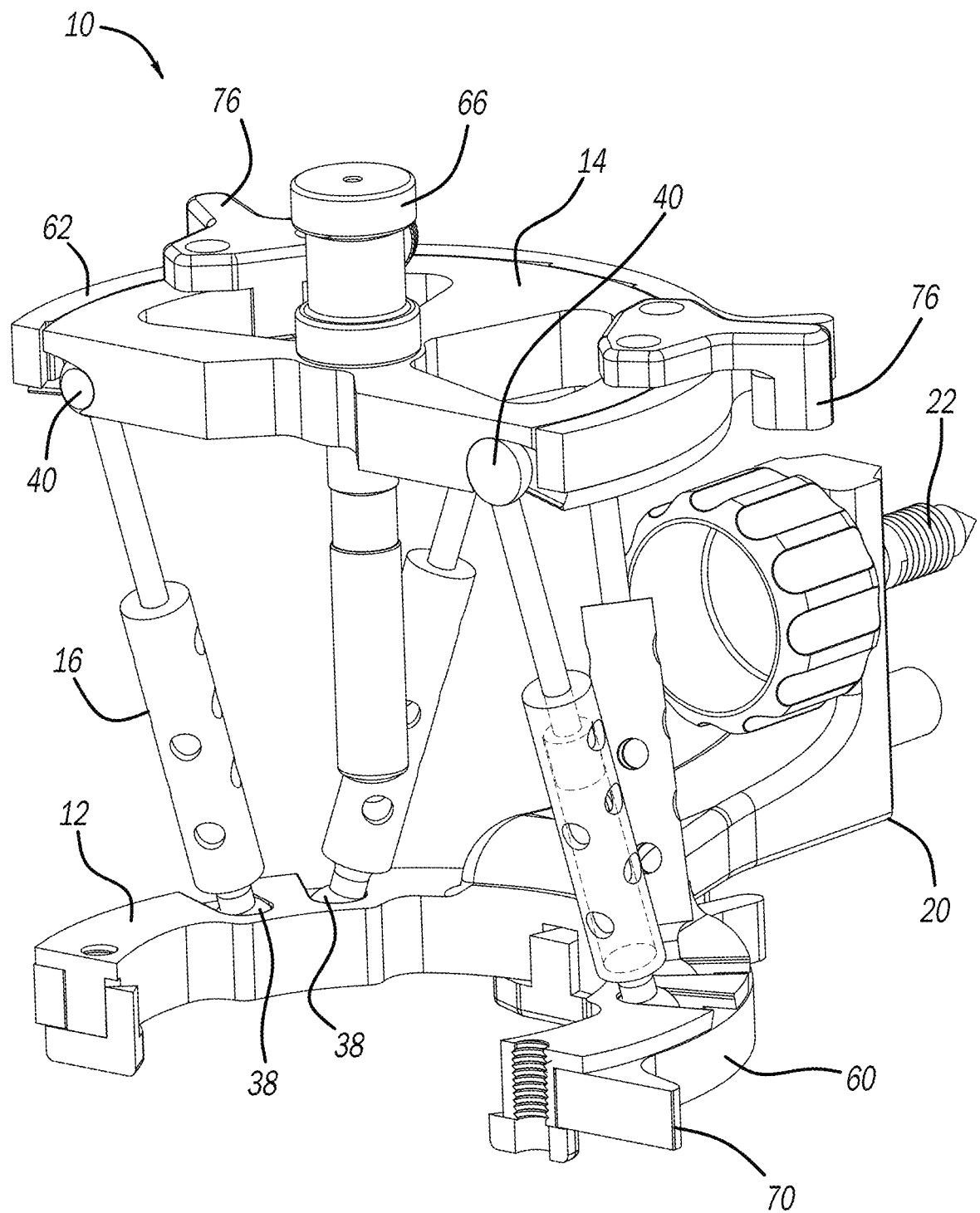
FIG. 6 is a cross-sectional view of the alignment device of FIG. 1A.

The guide locking ring 62 is substantially similar to the base locking ring 60. The guide locking ring 62 is rotatable about the guide 14 in both a first direction and a second direction, which is opposite to the first direction. The guide locking ring 62 includes a plurality of guide tabs 74, which may be pushed by a user to rotate the guide locking ring 62. Spaced apart about the guide 14 are stationary guide stops 76. The guide locking ring 62 is rotatable in the first direction until at least one of the guide tabs 74 contact an adjacent guide stop 76. The guide stops 76 are positioned such that when one (or more) of the guide tabs 74 contacts a guide stop 76, there is always another guide tab 74 that is spaced apart from a different guide stop 76. The guide tab 74 spaced apart from the different guide stop 76 may be pushed to rotate the guide locking ring 62 in the second (opposite) direction. More specifically and as illustrated in FIG. 1, the guide stops 76 and the guide tabs 74 are positioned such that when a first one of the guide tabs 74' is in contact with a first one of the guide stops 76', another one of the guide tabs 74" is spaced apart from another one of the guide stops 76" to facilitate rotation in an opposite direction.

Each one of the base spheres 38 of the linear actuator 16 is received by, and is in cooperation with, the base 12 at base joints 50, which include base locking arrangements 80A. Similarly, each one of the guide spheres 40 is received by, and is in cooperation with, the guide 14 at guide joints 52, which include guide locking arrangements 80B. The base locking arrangements 80A are the same as, or substantially similar to, the guide locking arrangements 80B. Thus, the following description of the base locking arrangement 80A also applies to the guide locking arrangements 80B.

Figure 7A:
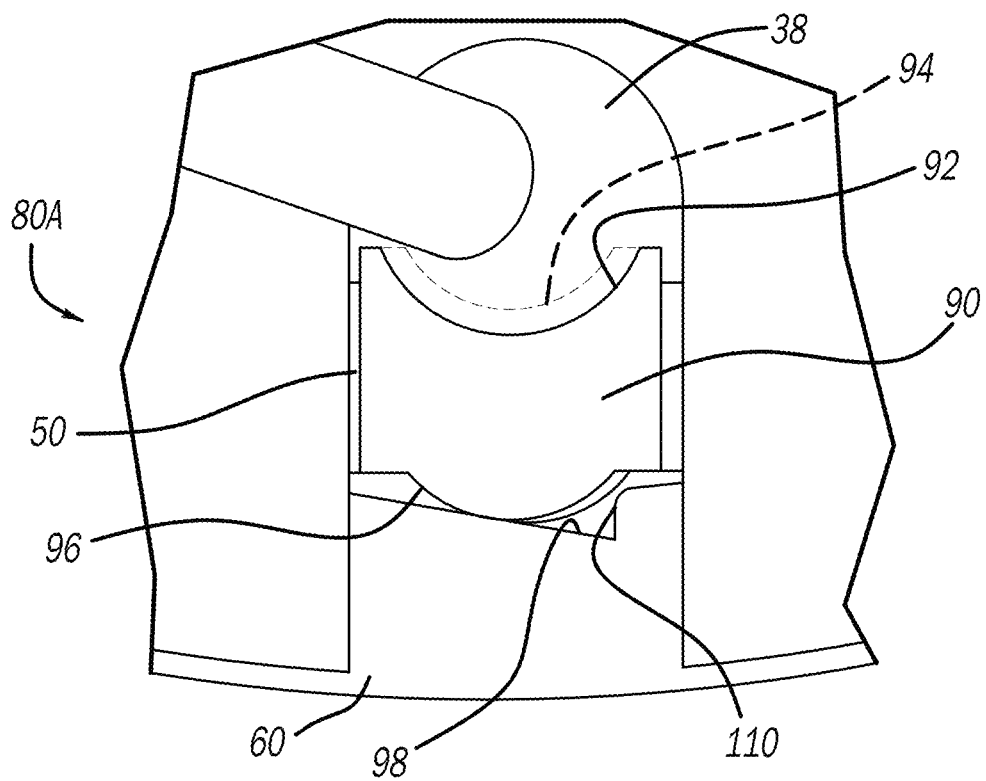
FIG. 7A illustrates an exemplary locking arrangement of the alignment device of FIG. 1A in an unlocked configuration.
Figure 7B:
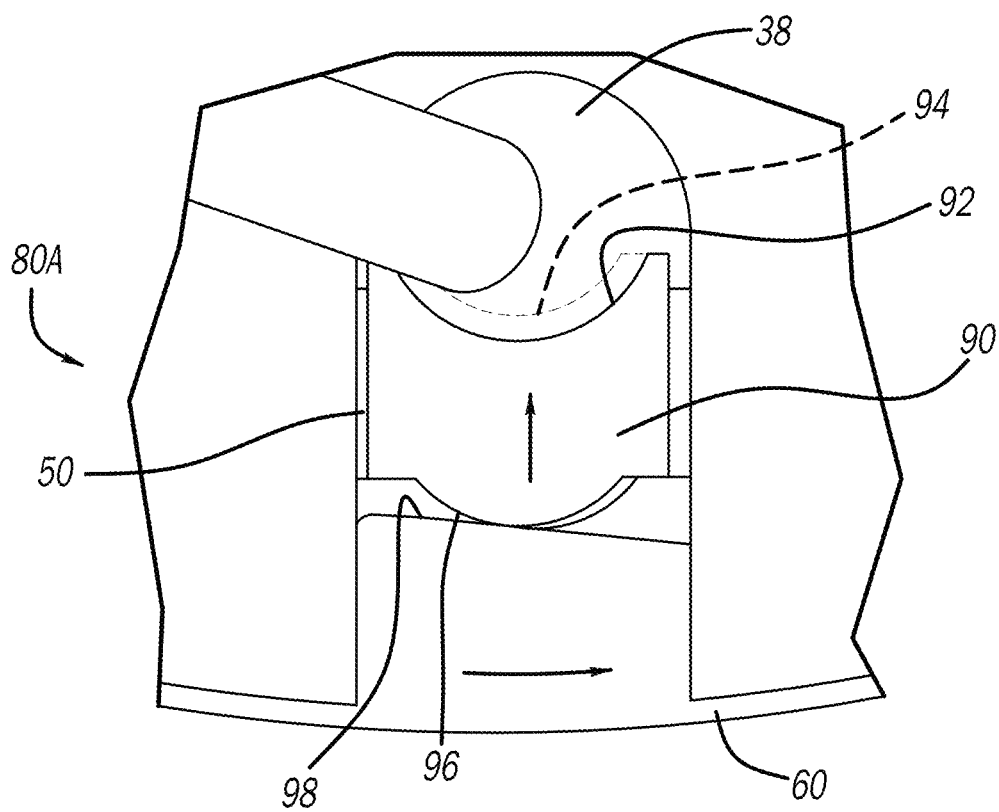
FIG. 7B illustrates the locking arrangement of FIG. 7A in a locked configuration.

With particular reference to FIGS. 7A and 7B, an exemplary one of the base locking arrangements 80A will now be described in detail. The description of the base locking arrangement 80A of FIGS. 7A and 7B also applies to all of the other base locking arrangements 80A, as well as to all of the guide locking arrangements 80B.

Each one of the base locking arrangements 80A includes a base brake 90. Similarly, each one of the guide locking arrangements 80B includes a guide brake. The following description of the base brake 90 also applies to all of the guide brakes. The base brake 90 defines a receptacle 92 configured to receive the base sphere 38. The receptacle 92 may be covered with any suitable friction-promoting insert or friction-promoting surface treatment 94 in order to enhance friction between the base brake 90 and the sphere 38.

Opposite to the receptacle 92, the base brake 90 includes a curved surface 96. The curved surface 96 is opposite to the base locking ring 60. In the unlocked position of FIG. 7A, the curved surface 96 is opposite to a base ramp 98 of the base locking ring 60. The base ramp 98 is angled such that a low end is adjacent to a flange 110, and a high end is opposite to the low end and the flange 110. In the unlocked position of FIG. 7A, the base brake 90 does not contact the base sphere 38 (or only lightly contacts the base sphere 38) to allow the base sphere 38 to freely rotate within the base joint 50. When all of the base locking arrangements 80A and the guide locking arrangements 80B are in the unlocked position, the base spheres 38 and the guide spheres 40 freely pivot within the base joints 50 and the guide joints 52 respectively to allow the guide 14 to be moved throughout six degrees of freedom relative to the base 12, which allows the guide 14 to be positioned at any suitable orientation.

After the guide 14 has been moved to a desired orientation, the base locking ring 60 and the guide locking ring 62 are rotated to lock the base joints 50 and the guide joints 52 respectively. Specifically, and as illustrated in FIG. 7B, rotation of the base locking ring 60 in a first direction moves the ramped surface 98 to the right in the orientation illustrated so that the relatively higher end of the base ramp 98 contacts the curved surface 96. The higher end of the base ramp 98 forces the base brake 90 into cooperation with the sphere 38. Cooperation between the sphere 38 and the friction promoting insert or surface treatment 94 of the base brake 90 prevents the sphere 38 from rotating, and thus locks the linear actuator 16. Similarly, rotation of the guide locking ring 62 in a first direction locks each one of the guide joints 52, thereby further restricting movement of the linear actuator 16 and locking the surgical alignment device 10 in a desired position for guiding any suitable instrument to a surgical site.

To unlock the device 10 and allow the position of the guide 14 to be readjusted, the base locking ring 60 and the guide locking ring 62 are rotated in a second direction, which is opposite to the first direction. Rotation of the base locking ring 60 in the second direction moves the base locking ring 60 back to the unlocked position of FIG. 7A, which results in the base brake 90 no longer applying a friction lock to the sphere 38. Similarly, rotation of the guide locking ring 62 in the second direction unlocks the guide joints 52. Thus, all of the base joints 50 may be locked and unlocked simultaneously using one hand, and all of the guide joints 52 may be locked and unlocked simultaneously using one hand.

The base locking arrangement 80A and the guide locking arrangement 80B are merely exemplary locking arrangements. One skilled in the art will appreciate that any other suitable locking arrangements may be implemented. For example, electromagnets may be included to move the base brake 90 and the guide brake to the locked and unlocked positions. One skilled in the art will appreciate that any other suitable locking mechanisms may be used that provide for one-hand locking operation. The present disclosure thus advantageously provides for the surgical alignment device 10, which may be locked and unlocked using only one hand.

An exemplary procedure using the device 10 at an exemplary surgical site 210 including a skull and brain will now be described with reference to FIG. 1A, for example. The surgical site 210 is prepared and mapped to determine where to position the instrument 310, and thus the device 10. The device 10 is anchored in any suitable manner, such as by way of the connector 18 or any other suitable mounting device/assembly. In some applications, the device 10 may be anchored directly to the skull or other bone. For example, the base 12 may be anchored directly to the skull using any suitable screw, pin, etc. Before and/or after the device 10 is mounted at the skull 210, the guide 14 is positioned relative to the base 12 to orient the guide 14 to direct the instrument 310 to the surgical site 210 at a desired angle or trajectory. Once the orientation or trajectory is set, the device 10 is locked as described above by rotating the base locking ring 60 and/or the guide locking ring 62, which locks the guide 14 relative to the base 12. As explained above, the base locking ring 60 and the guide locking ring 62 may advantageously be locked using only one hand. The instrument or implant 310 is then directed to the surgical site 210 through the instrument guide 66 to perform the desired procedure.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected, or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer, or section. Terms such as "first," "second," and other numerical terms when used herein do not imply a sequence or order unless clearly indicated by the context. Thus, a first element, component, region, layer, or section discussed below could be termed a second element, component, region, layer, or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A surgical alignment device comprising:
   a base;
   a guide;
   a plurality of linear actuators each extending between the base and the guide, the plurality of linear actuators including first ends connected to the base at base joints and second ends connected to the guide at guide joints; and
   a locking arrangement configured to simultaneously lock all of the base joints or simultaneously lock all of the guide joints;
   wherein the locking arrangement is configured to simultaneously directly engage all of the base joints or all of the guide joints;
   wherein the locking arrangement is configured to allow all of the base joints or all of the guide joints to freely pivot to allow the guide to be move throughout the six degrees of freedom relative to the base to allow the guide to be positioned at any suitable orientation.

2. The surgical alignment device of claim 1, wherein the locking arrangement includes a base locking arrangement configured to simultaneously lock all of the base joints, and a guide locking arrangement configured to simultaneously lock all of the guide joints.

3. The surgical alignment device of claim 1, wherein the locking arrangement includes a base locking arrangement at the base, the base locking arrangement including base brakes at each one of the base joints, the base brakes simultaneously movable to simultaneously lock each one of the base joints.

4. The surgical alignment device of claim 3, further comprising a base locking ring, rotation of the base locking ring in a first direction simultaneously moves the base brakes into cooperation with base spheres of the base joints to simultaneously lock the base joints, and rotation of the base locking ring in a second direction opposite to the first direction simultaneously releases the base brakes from cooperation with the base spheres to simultaneously unlock the base joints.

5. The surgical alignment device of claim 1, wherein the locking arrangement includes a guide locking arrangement at the guide, the guide locking arrangement including guide brakes at each one of the guide joints, the guide brakes simultaneously movable to simultaneously lock each one of the guide joints.

6. The surgical alignment device of claim 5, further comprising a guide locking ring, rotation of the guide locking ring in a first direction simultaneously moves the guide brakes into cooperation with guide spheres of the guide joints to simultaneously lock the guide joints, and rotation of the guide locking ring in a second direction opposite to the first direction simultaneously releases the guide brakes from cooperation with the guide spheres to simultaneously unlock the guide joints.

7. The surgical alignment device of claim 1, wherein each one of the plurality of linear actuators is configured to extend and contract.

8. The surgical alignment device of claim 7, wherein the plurality of linear actuators, the base joints, and the guide joints are configured to together provide six degrees of freedom movement of the guide relative to the base.

9. The surgical alignment device of claim 1, wherein the plurality of linear actuators includes six linear actuators.

10. The surgical alignment device of claim 1, wherein the guide defines an aperture at a center thereof configured to receive a surgical instrument for guiding the surgical instrument to a surgical site.

11. A surgical alignment device comprising:
a base;
a guide;
a plurality of linear actuators each extending between the base and the guide, the plurality of linear actuators including first ends connected to the base at base joints and second ends connected to the guide at guide joints;
a base brake at each one of the base joints;
a guide brake at each one of the guide joints;
a base locking ring included with the base and in cooperation with each of the base brakes such that rotation of the base locking ring in a first direction simultaneously moves each of the base brakes into direct engagement with each of the base joints to simultaneously lock each of the base joints, and rotation of the base locking ring in a second direction opposite to the first direction simultaneously releases each of the base brakes from engagement with each of the base joints to simultaneously unlock each of the base joints; and
a guide locking ring included with the guide and in cooperation with each of the guide brakes such that rotation of the guide locking ring in a first direction simultaneously moves each of the guide brakes into direct engagement with each of the guide joints to simultaneously lock each of the guide joints, and rotation of the guide locking ring in a second direction opposite to the first direction simultaneously releases each of the guide brakes from engagement with each pf the guide joints to simultaneously unlock each of the guide joints;
wherein the guide is freely movable throughout six degrees of freedom relative to the base to allow the guide to be positioned at any suitable orientation.

12. The surgical alignment device of claim 11, wherein each one of the plurality of linear actuators is configured to extend and contract.

13. The surgical alignment device of claim 12, wherein the plurality of linear actuators, the base joints, and the guide joints are configured to together provide six degrees of freedom movement of the guide relative to the base.

14. The surgical alignment device of claim 11, wherein the plurality of linear actuators includes six linear actuators.

15. The surgical alignment device of claim 11, wherein the guide defines an aperture at a center thereof configured to receive a surgical instrument for guiding the surgical instrument to a surgical site.

16. The surgical alignment device of claim 11, wherein each one of the base brakes and each one of the guide brakes includes:
a receptacle configured to receive a sphere of each one of the base joints and each one of the guide joints respectively, the receptacle including a friction promoting insert or surface treatment; and
a curved surface opposite to the receptacle.

17. A surgical alignment device comprising:
a base:
a guide:
a plurality of linear actuators each extending between the base and the guide, the plurality of linear actuators including first ends connected to the base at base joints and second ends connected to the guide at guide joints;
base brakes at each one of the base joints;
guide brakes at each one of the guide joints;
a base locking ring included with the base and in cooperation with the base brakes such that rotation of the base locking ring in a first direction moves the base brakes into engagement with the plurality of linear actuators to lock the base joints, and rotation of the base locking ring in a second direction opposite to the first direction releases the base brakes from engagement with the plurality of linear actuators to unlock the base joints;
a guide locking ring included with the guide and in cooperation with the guide brakes such that rotation of the guide locking ring in a first direction moves the guide brakes into engagement with the plurality of linear actuators to lock the guide joints, and rotation of the guide locking ring in a second direction opposite to the first direction releases the guide brakes from engagement with the plurality of linear actuators to unlock the guide joints;
wherein each one of the base brakes and each one of the guide brakes includes:
a receptacle configured to receive a sphere of each one of the base joints and each one of the guide joints respectively, the receptacle including a friction promoting insert or surface treatment; and
a curved surface opposite to the receptacle;
the base locking ring includes a plurality of base ramps, each one of the plurality of base ramps is in cooperation with one of the curved surfaces of one of the base brakes; and
the guide locking ring includes a plurality of guide ramps, each one of the plurality of guide ramps is in cooperation with one of the curved surfaces of one of the guide brakes.

18. The surgical alignment device of claim 17, wherein:
rotation of the base locking ring in the first direction moves the plurality of base ramps relative to the curved surfaces of the base brakes such that relatively high ends of the base ramps contact the curved surfaces to force the base brakes into cooperation with the spheres of each of the base joints to lock the base joints; and
rotation of the guide locking ring in the first direction moves the plurality of guide ramps relative to the curved surfaces of the guide brakes such that relatively high ends of the guide ramps contact the curved surfaces to force the guide brakes into cooperation with the spheres of each of the guide joints to lock the guide joints.

19. The surgical alignment device of claim 18, wherein:
rotation of the base locking ring in the second direction moves the plurality of base ramps relative to the curved surfaces of the base brakes such that relatively low ends of the base ramps contact the curved surfaces to release the base brakes from cooperation with the spheres of each of the base joints to unlock the base joints; and
rotation of the guide locking ring in the second direction moves the plurality of guide ramps relative to the curved surfaces of the guide brakes such that relatively low ends of the guide ramps contact the curved surfaces to release the guide brakes from cooperation with the spheres of each of the guide joints to lock the guide joints.

* * * * *